(12) United States Patent
Nahas et al.

(10) Patent No.: US 6,248,530 B1
(45) Date of Patent: Jun. 19, 2001

(54) METHOD FOR ELIMINATING SPECIFIC SEQUENCES WHEN CONSTRUCTING DNA LIBRARIES

(75) Inventors: Nasri Nahas; Jean-Baptiste Dumas Milne Edwards, both of Paris (FR)

(73) Assignee: Genset, S.A., Paris (FR)

( * ) Notice: Subject to any disclaimer, the term of this patent is extended or adjusted under 35 U.S.C. 154(b) by 0 days.

(21) Appl. No.: 09/331,709

(22) PCT Filed: Dec. 22, 1997

(86) PCT No.: PCT/FR97/02378

§ 371 Date: Jul. 23, 1999

§ 102(e) Date: Jul. 23, 1999

(87) PCT Pub. No.: WO98/28439

PCT Pub. Date: Jul. 2, 1998

(30) Foreign Application Priority Data

Dec. 23, 1996 (FR) .................................................. 96 15854

(51) Int. Cl.[7] .............................. C12Q 1/68; C07H 19/00; C07H 21/00; C07H 21/04
(52) U.S. Cl. .............................. 435/6; 536/23.1; 536/24.3
(58) Field of Search .................................. 435/91.1, 91.4, 435/91.5, 91.51, 320.1, 455, 463; 514/44; 536/18.5, 23.1, 24.3, 24.31, 24.33, 24.5, 25.3; 935/1–5, 36, 38, 56

(56) References Cited

U.S. PATENT DOCUMENTS 5,500,356 * 3/1996 Li et al. ............................... 435/91.1
5,801,154 * 9/1998 Baracchini et al. .................... 514/44

OTHER PUBLICATIONS

Heineman et al. 1994, Jour. of Virology vol. 68 (5), pp. 3317–3323.*

Honigberg et al. 1986, Proc Nat'l Acad. Sci. vol. 83, pp. 9586–9590.*

Teintze, et al. 1995, Biochem. & Biophys. Research Communi vol. 211 (3), pp. 804–811.*

Sambrook et al. Molecular Cloning, A Lab–Manual 2nd Ed. 1989. Cold Spring Harbor Lab Press.*

Soares, et al., *Proc. Natl. Acad. Sci. USA*, vol. 91, pp. 9228–9232, Sep. 1994. "Construction and characterization of a normalized cDNA library".

Sasaki et al., *Nucleic Acids Research*, vol. 22, No. 6, pp. 987–992, 1994 "Construction of a normalized cDNA library by introduction of a semi–solid mRNA–cDNA hybridzation system".

Lanfranchi, et al., *Genome Research*, vol. 6, pp. 35–42, 1996 "Identification of 4370 Expressed Sequence Tags from a 3'–End–Specific cDNA Library of Human Skeletal Muscle by DNA Sequencing and Filter Hybridization".

* cited by examiner

*Primary Examiner*—Remy Yucel
*Assistant Examiner*—Jane Zara
(74) *Attorney, Agent, or Firm*—Knobbe, Martens, Olson & Bear, LLP

(57) ABSTRACT

The invention concerns a method for specifically eliminating at least one type of double strand DNA plasmid from a set of plasmids, characterised in that it consists in: preparing presynaptic filaments by fixing a protein with RecA activity on a single strand DNA whose sequence corresponds to a sequence of the plasmid to be eliminated and which further comprises a recognition sequence for a restriction enzyme sensitive to methylation; mixing the set of plasmid with the presynaptic filaments to form triplexes on the plasmids with the presynaptic filaments to form triplexes on the plasmids to be eliminated; methylating the resulting DNA mixture; releasing the triplexes; digesting the mixture obtained with the restriction methylation sensitive enzyme; if necessary, eliminating or separating the linear double strand DNA's corresponding to the plasmids to be eliminated. The method is useful for preparing DNAc libraries.

33 Claims, 4 Drawing Sheets

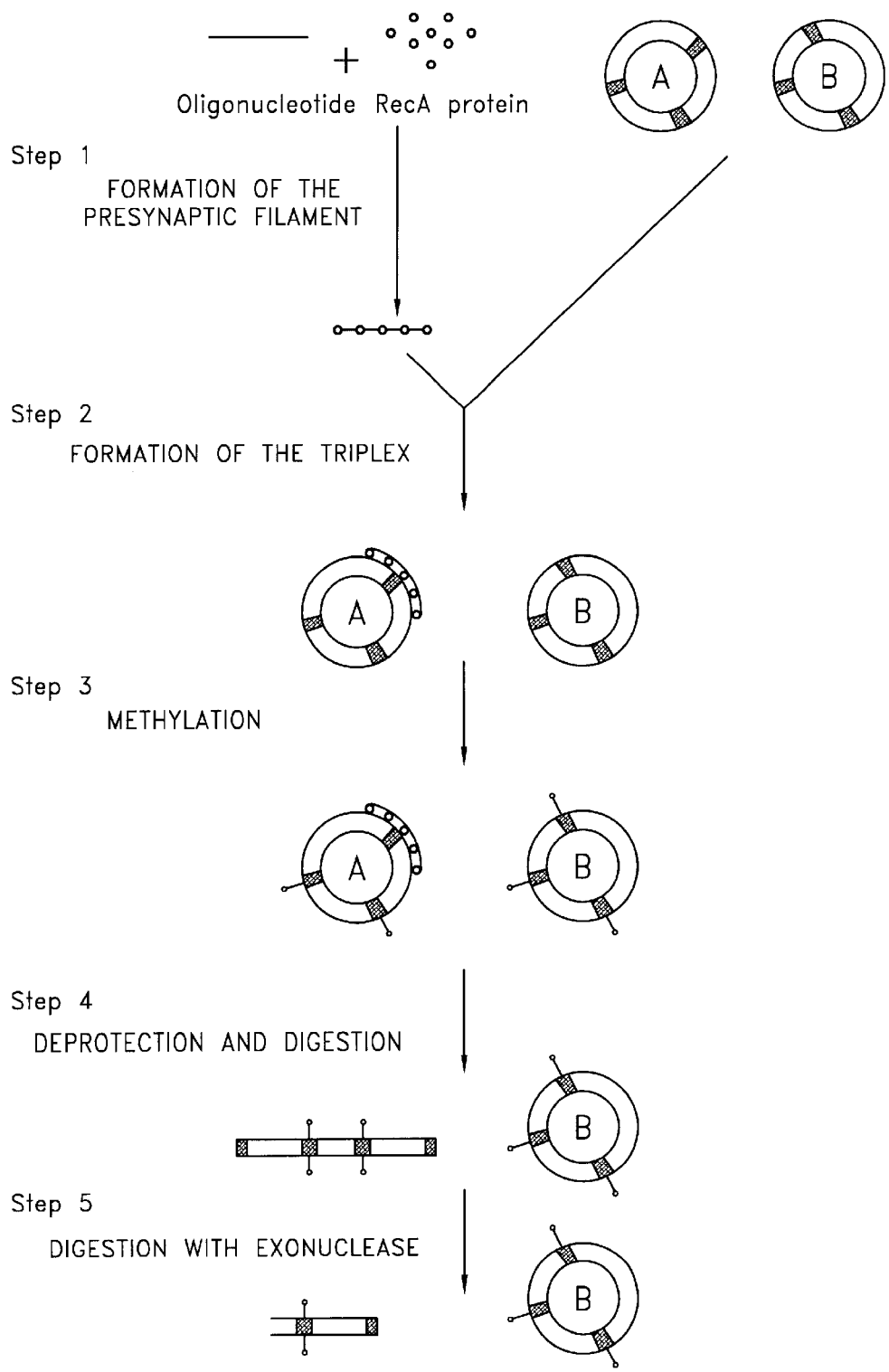

Figure 2A:
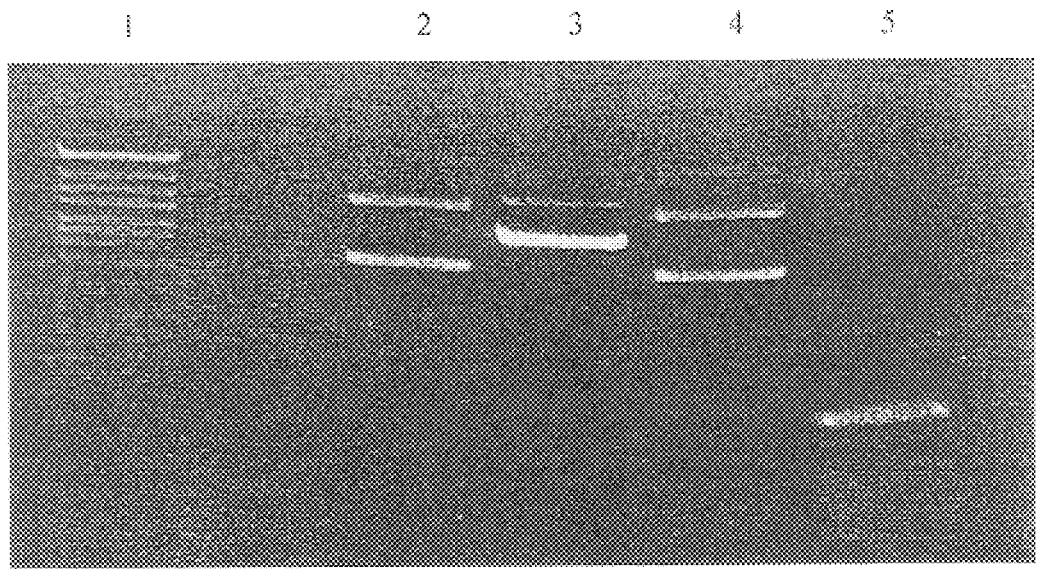

CLONE 1 (SEQ ID NO : 1) :

```
aatcacaaaa ctcatgatgc tccggctgct cagttgtgg  ctccttgtgg ccgttgcctc  60
aggctatggc ccaccttcct ctcgcccttc cagccgcgtt gtcaatggtg aggatgcggt  120
ccctacagc  tggccctggc aggtttccct gcagtatgag aaaagtggaa gcttctacca  180
cacgtgtggc ggtagcctca tcgscccga  ttgggttgtg actgccggcc actgcatctc  240
gagggatctg acctaccagg tggtgttggg tgagtacaac cttgctgtga aggagggccc  300
cgagcaggtg atccccatca actctgagga gctgttttgt catccactct ggaaccgctc  360
gtgtgtngcc tgtgcaatg  acatcgccct catcaagctc tcacgcagcg cccagctggg  420
agatgccgtc cagctcgcct cacccctcc  cgctggtgac atccttccca acaagacacc  480
ctgctacatc acggctggg  gccgtctcta taccaatggg ccactcccag acaagctgca  540
gcaggcccgg ctgccgtgg  tggactataa gcactgctcc aggtggaact ggtgggttc   600
caccgtgaag aaaaccatgg tgtgtgctgg agggtacatc cgctccggct gcaacggtga  660
ctctggagga cccctcaact gccccacaga ggatggtggc tggcaggtcc acggtgtgac  720
cagctttgtt tctggctttg gctgcaactt catctggamg cccwccgg              769
```

CLONE 13 (SEQ ID NO : 2) :

```
atggactcca ggaaaaccca tggccatgag gttgatcctg ttttttggtg cccttttttgg  60
gcatatctac tgtctagaaa catttgtggg agaccaagtt cttgagattg taccaagcaa  120
tgaagaacaa attaaaaatc tgctacaatt ggaggctctaa gaacatctcc agcttgattt  180
ttggaaatca cccaccaccc cagggagaca gcccacgtcc gagttcccctt cgtcaacgtc  240
caggcagtca aagtgttctt ggagtccag  ggaattgcct attccatcat gattgaagac  300
gtgcaggtcc tgtttggacaa agagaatgaa gaaatgcttt ttaataggag aagagaacgg  360
agtggtaact tcaattttgg ggcctaccat acctggaag  agatttccca agaaaatggat  420
aacctcgtgg ctgagcaccc tggtctagtg agcaaagtga accggaggag atattggctc  480
aaccggccta tgaacgtgct caagttcagc caagccagc  acaagccagc ttcttttgag tatctggctg  540
gatgctggga agagtgggtt agagtggggt acacaaaghwa csvcaccaad g            591
```

*Fig. 4*

SEQUENCE LISTING

```
<160> NUMBER OF SEQ ID NOS:  4

<210> SEQ ID NO 1
<211> LENGTH: 769
<212> TYPE: DNA
<213> ORGANISM: Homo sapien
<220> FEATURE:
<221> NAME/KEY: misc_feature
<222> LOCATION: (1)...(769)
<223> OTHER INFORMATION: n = A,T,C or G

<400> SEQUENCE: 1
aatcacaaaa ctcatgatgc tccggctgct cagttccctc ctccttgtgg ccgttgcctc      60
aggctatggc ccaccttcct ctcgcccttc cagccgcgtt gtcaatggtg aggatgcggt     120
cccctacagc tggccctggc aggtttccct gcagtatgag aaaagtggaa gcttctacca     180
cacgtgtggc ggtagcctca tcgsccccga ttgggttgtg actgccggcc actgcatctc     240
gagggatctg acctaccagg tggtgttggg tgagtacaac cttgctgtga aggagggccc     300
cgagcaggtg atccccatca actctgagga gctgtttgtg catccactct ggaaccgctc     360
gtgtgtngcc tgtggcaatg acatcgccct catcaagctc tcacgcagcg cccagctggg     420
agatgccgtc cagctcgcct cactccctcc cgctggtgac atccttccca acaagacacc     480
ctgctacatc accggctggg gccgtctcta taccaatggg ccactcccag acaagctgca     540
gcaggcccgg ctgcccgtgg tggactataa gcactgctcc aggtggaact ggtggggttc     600
caccgtgaag aaaaccatgg tgtgtgctgg agggtacatc cgctccggct gcaacggtga     660
ctctggagga cccctcaact gccccacaga ggatggtggc tggcaggtcc acggtgtgac     720
cagctttgtt tctggctttg gctgcaactt catctggamg cccwccggg                 769

<210> SEQ ID NO 2
<211> LENGTH: 591
<212> TYPE: DNA
<213> ORGANISM: Homo sapien

<400> SEQUENCE: 2
atggactcca ggaaaaccca tggccatgag gttgatcctg ttttttggtg ccctttttgg      60
gcatatctac tgtctagaaa catttgtggg agaccaagtt cttgagattg taccaagcaa     120
tgaagaacaa attaaaaatc tgctacaatt ggaggctcaa gaacatctcc agcttgattt     180
ttggaaatca cccaccaccc cagggagaca gcccacgtcc gagttccctt cgtcaacgtc     240
caggcagtca aagtgttctt ggagtcccag ggaattgcct attccatcat gattgaagac     300
gtgcaggtcc tgttggacaa agagaatgaa gaaatgcttt ttaataggag aagagaacgg     360
```

-continued

```
agtggtaact tcaattttgg ggcctaccat accctggaag agatttccca agaaatggat      420
aacctcgtgg ctgagcaccc tggtctagtg agcaaagtga atattggctc ttcttttgag      480
aaccggccta tgaacgtgct caagttcagc accggaggag acaagccagc tatctggctg      540
gatgctggga tccatgctcg agagtgggtt acacaaghwa csvcaccaad g                591

<210> SEQ ID NO 3
<211> LENGTH: 33
<212> TYPE: DNA
<213> ORGANISM: Artificial Sequence
<220> FEATURE:
<223> OTHER INFORMATION: Oligonucleotide

<400> SEQUENCE: 3
gatgctccgg ctgctcagtt ccctcctcct tgt                                    33

<210> SEQ ID NO 4
<211> LENGTH: 29
<212> TYPE: DNA
<213> ORGANISM: Artificial Sequence
<220> FEATURE:
<223> OTHER INFORMATION: Oligonucleotide

<400> SEQUENCE: 4
tcttttgaga accggcctat gaacgtgct                                         29
```

METHOD FOR ELIMINATING SPECIFIC SEQUENCES WHEN CONSTRUCTING DNA LIBRARIES

The present invention relates to a method intended in particular for eliminating specific sequences from DNA libraries.

The invention relates more particularly to a method for eliminating at least one specific, in particular abundant, sequence from a cDNA library.

The random sequencing of cDNA clones has been used for many years as a means for obtaining differential expression profiles and for discovering new sequences. Typically, it involves extracting the messenger RNAs (mRNA) of particular cells or tissues, cloning the corresponding cDNAs and then randomly selecting clones which will be sequenced. If the objective is the search for new sequences, the operation of exhaustive sequencing of a cDNA library is made expensive because of the repetitiveness of the mRNA population. Indeed, while, according to the tissues, 15,000 to 50,000 molecular species of mRNA are expressed, they represent a total of 200 to 500,000 molecules in cells (Davidson and Britten, 1979).

In the cells, the messengers are expressed at different levels according to the molecular species. Thus, 10 to 20 molecular species may represent 10 to 20% of molecules of mRNA. Many authors have studied the repetitiveness of libraries and have shown that, in some cases, only one molecular species could count for more than 20% of the clones. In order to clarify these data, the inventors studied the repetitiveness of mRNA sequences in several human tissues. For that, they classified by similarity groups the sequences of clones randomly selected from 5'-end libraries.

For 2 to 3000 clones sequenced, the fractions of clones belonging to similarity groups containing 10 sequences or more are, respectively, 39%, 6.8%, 22%, 54%, 34%, 46%, 27%, 27%, 7% and 39%, for tissues or cells such as the placenta, brain, spleen, pancreas, colon, lymphocytes, liver, kidney, ovary and heart (Table I).

TABLE I

| TISSUES | % TOP15 | % TOP20 | % TOP30 |
|---|---|---|---|
| Pancreas | 46 | 48 | 52 |
| Kidney [sic] | 15 | 17 | 20 |
| Colon | 18 | 21 | 26 |
| Lymphocyte | 25 | 28 | 33 |
| Kidney | 23 | 26 | 30.5 |
| Dystrophic muscle | 26 | 27.5 | 31.5 |
| Liver | 27 | 29 | 33 |
| Ovary | 7.5 | 8 | 10 |
| Brain | 8 | 9 | 11 |

Table I: Abundance profile for the clones most widely represented in tagged cDNA libraries. The libraries are constructed from messenger RNAs from the: pancreas, spleen, colon, lymphocyte, kidney, dystrophic muscle, liver, ovary and brain. The table shows the distribution of the 15, 20 or 30 clones most widely represented in each of our libraries.

Thus, the cost of a new sequence may be very high; indeed, between a quarter and half of the sequences have already been produced very rapidly during the sequencing. For each sequence, there is therefore a between 50 and 75% chance that this sequence has already been made. To limit the cost of new sequences, several solutions have been proposed.

The first consists in normalizing the cDNA libraries or the starting mRNA population. This consists in reducing the frequency of the abundant sequences so that it is near the frequency of the rare sequences. Several normalization methods have been proposed. One of them consists in using the genomic DNA as normalization template (Weisman, 1987). In this case, the distribution of the cDNA clones obtained should be correlated with the number of exons in the gene.

The normalization method most widely used is based on the kinetics of hybridization. When a population of nucleic acids is denatured, the rate of renaturation (or of reannealing of the molecules) is proportional to the number of molecular species present. In other words, the higher the number of molecular species present in the cDNA population, the greater the rate of renaturation of the corresponding cDNA molecules (Britten et al., 1974; Young & Anderson, 1985). The principal technical difficulty of this approach is to correctly separate the populations of annealed molecules from the populations of nonannealed molecules.

Most of the methods involve a chromatography on hydroxyapatite resin which releases the single-strand molecules and the double-strand molecules at different concentrations of phosphate ions (Patanjali et al., 1991). Strategies involving semisolid systems for eliminating DNA—DNA duplexes or DNA-RNA heteroduplexes have been recently proposed (Sasaki et al., 1994). In this case, cDNAs are synthesized with the aid of primers to which latex beads have been attached at the 5' end. The cDNA populations obtained are used as hybridization template with an mRNA population and the heteroduplexes are collected by centrifugation.

All the techniques for normalization by hybridization have the limitation of not allowing discrimination between weakly divergent sequences. Recently, Bento Soares (Soares et al., 1994; Soares & Efstratiadis, 1995) has proposed a method which makes it possible to subtract the abundant sequences from the cDNA libraries. This method is based on the mass production of single-strand plasmids from a cDNA library produced by priming anchored on the poly-A tail of the mRNAs. The defined end thus obtained is used to prime the synthesis of short segments of DNA on the single-strand plasmid template. This makes it possible to obtain molecules which are locally double-stranded. The small size of the neosynthesized fragment (200±20-nt) is an advantage in the subtraction strategy because the 3'-untranslated sequences are much more divergent than the coding sequences. Furthermore, since all the fragments have roughly the same size, the kinetics of hybridization for the entire plasmid population is simpler. Subsequently, the normalization of the library is carried out by denaturing the duplexes and by exploiting their different rehybridization kinetics. The separation of the single-strand circular plasmids and of the heteroduplexes is carried out by means of hydroxyapatite columns. The single-strand plasmids are then converted to a double-strand by primer extension and transfected into bacteria. This method has the advantage of placing the hybridization partners under equimolar condition; on the other hand, it has two disadvantages:
  1) the purification of the nonrecombinant clones,
  2) for a good hybridization, the size of the fragment neosynthesized from the single-strand circular plasmids should be approximately 200 nt.

In the case of the 5'-end libraries produced here, the average size of the inserts is 200 to 250 nt. Thus, the Soares normalization strategy is hardly applicable.

The second solution proposed for limiting the cost of new sequences consists in ordering the cDNA library on filters and in hybridizing the filters with probes corresponding to the most abundant messengers and then in ordering, in a microtiter plate, the clones which are not identified by the probe. The choice of the most abundant groups of sequences may be made by analyzing a few thousand clones (Lanfranchi et al., 1985), or alternatively by using probes consisting of the total cDNA, the mitochondrial genome and/or a few specific clones chosen for their great abundance (Adams et al., 1995). This approach may be attractive because, unlike normalization, it allows the location and then the elimination, by virtue of the selection of nonrecognized clones, of the clones corresponding to the most abundant sequences.

However, the manipulations for ordering the clones on a filter and for hybridization are cumbersome and the selection of the clones not recognized by the probes used is often delicate (hybridization background noise, precise identification of the clones, possible errors during the reordering and the subcloning of the library).

In the present invention, the elimination is carried out by making unclonable the plasmids having inserts corresponding to the targeted specific sequences which are among the most abundant. This is carried out by selectively directing the activity of restriction enzymes to the sequences to be eliminated. The clones thus linearized are no longer capable of transforming bacteria.

Accordingly, the present invention relates to a method for specifically eliminating at least one type of double-strand DNA plasmid from a set of plasmids in particular in the case of the creation of a library, characterized in that:

fragments of nucleic acids are prepared which are capable of forming triplex structures and whose sequence corresponds to a sequence of the plasmid, more particularly to a fragment of the sequence of the group of clones to be eliminated and which further comprises a recognition site for a restriction enzyme sensitive to methylation;

the set of plasmids is mixed with said fragments of nucleic acids to form triplexes on the plasmids to be eliminated;

the DNA mixture obtained is methylated;

the triplexes are released;

the mixture obtained is digested with the methylation-sensitive restriction enzyme;

if necessary, the linear double-strand DNAs corresponding to the plasmids to be eliminated are eliminated or separated.

In a first embodiment, the formation of the triplex will be carried out by hybridization of a presynaptic filament with the target sequence, in the presence of a protein with RecA activity.

This method is derived from the so-called "Achilles Heel" strategy described by Koob et al. (1992), used for linear DNA sequences.

In this method, the binding of a protein, in particular the RecA protein, to an appropriate single-strand DNA molecule catalyzes the formation of a triplex between this single-strand DNA (oligonucleotide) and a corresponding double-strand DNA; the triplex thus formed protects the sequences involved therein from methylation.

When the triplexes are released, the corresponding, nonmethylated, sequences become the only ones which are sensitive to the specific restriction enzymes chosen. There are thus obtained in the mixture circular plasmids and linear DNAs corresponding to the plasmids which it is desired to eliminate, which may be carried out in various ways as will be explicitly stated hereinafter.

More particularly, the schematic representation of the invention applied to circular double-strand plasmid DNA of a cDNA library is represented in FIG. 1.

The method according to the present invention can be more particularly used when the set of starting plasmids constitutes a cDNA library, as was mentioned above.

The method can in particular be used for the elimination of a clone carrying a known specific sequence.

In the first step, that is to say the formation of the presynaptic filament, it is possible to use the RecA protein which is known to bind to single-strand DNA (oligonucleotide) and to form said presynaptic filament, but it is also possible to use other proteins, in particular a so-called protein "with RecA activity" which will be defined hereinafter as being capable of participating in the formation of a presynaptic filament which will protect the targeted double-strand DNA sequence from methylation by forming a triplex with it.

This first step of forming the presynaptic filament requires the hydrolysis of ATP or of its modified homolog ($\gamma$S)ATP.

Of course, the selection of the single-strand DNA used to form the presynaptic filament (oligonucleotide) constitutes one of the key elements of the present invention since it will be necessary to choose the sequence of this oligonucleotide from the sequence(s) of the clone(s) which it is desired to eliminate, and since this sequence must contain a recognition site for a restriction enzyme "sensitive to methylation". "Restriction enzyme sensitive to methylation" is understood to mean a restriction enzyme which recognizes its site when the latter is not methylated. Among the enzymes which may be used, there should be mentioned in particular the enzymes cited in Table II and more particularly the enzymes HaeIII and MspI.

The oligonucleotides used for the formation of the presynaptic filament will be preferably oligonucleotides containing about 30 nucleotides.

TABLE II

LIST OF THE ENZYMES WHICH CAN BE USED IN THE PROCEDURE FOR THE ELIMINATION OF ONE OR MORE SPECIFIC, IN PARTICULAR ABUNDANT, CLONES FROM A DNA LIBRARY
(nonlimiting list)

I. Methylases

.M.BamHI
.M.EcoRI
.M.pstI
.M.ClaI
.M.HaeIII
.M.MspI
.M.HhaI
.M.HpaI
.CpG Methylase (methylates the C residues of dinucleotides (5'. . . . . CG . . . . . 3'. Among the restriction enzymes cited below, this methylase affects the following: AciI, BstUI, ClaI, HhaI, HinPI and MspI).

II. 6-base restriction enzymes

.BamHI
.EcoRI
.PstI
.ClaI

III. 4-base restriction enzymes

.HaeIII
.MspI
.HhaI
.HpaI
.AciI

TABLE II-continued

LIST OF THE ENZYMES WHICH CAN BE USED IN THE PROCEDURE FOR THE ELIMINATION OF ONE OR MORE SPECIFIC, IN PARTICULAR ABUNDANT, CLONES FROM A DNA LIBRARY
(nonlimiting list)

.BstUI
.HinPI

During the second step, the presynaptic filament thus formed is mixed with the double-strand DNA, in this case the plasmids into which the sequences of the library have been cloned, under conditions which make it possible to form a stable DNA triplex, this being in the presence of (γS)ATP. The reaction is also carried out in the presence of a divalent cation, in particular Mg2++.

The RecA protein alters the topology of the DNA double helix and allows the presynaptic filament, in the present case the oligonucleotide [sic], access to its complementary sequence on the double-strand DNA of the clones to be eliminated. The complex is stabilized during this step.

It should be noted that no strand exchange is possible between the presynaptic filament and the double-strand DNA. Indeed, such an event would require a high efficiency of hydrolysis which cannot be achieved because of the use of (γS)ATP whose hydrolysis efficiency is 100 times lower than that of ATP. Under these conditions, the DNA triplex remains stable and can be stored for several days at −20° C.

In a second embodiment, the triplexes will be formed over the regions to be protected from methylation, by hybridization of the target sequences with PNAs, "Peptide Nucleic Acids" (Veselkov et al., 1996).

The third step consists in methylating the DNA mixture consisting of double-strand DNA molecules containing locally, for some, regions involved in triplexes.

To do this, methyltransferases are used to specifically methylate the recognition sites for the restriction enzymes which have been chosen.

This step is of course important because it protects from cleavage by restriction enzymes other sites which may be present elsewhere in the inserts from the library and in the cloning vector.

The specific regions which correspond to the clones which it is desired to eliminate are in principle protected from methylation by the formation of the triplex. These regions will therefore not be methylated and will be subsequently the only ones recognized by the corresponding restriction enzyme.

In the next step, the triplexes are released, either by denaturing the protein with RecA activity, in particular RecA, or by denaturing the triplexes formed with the PNAs. A mixture of double-strand circular plasmids is thus obtained. At the end of this step, some of the plasmids contain regions which are not methylated because they correspond to the regions protected by the triplex.

In the fourth step, the mixture obtained is digested with the methylation-sensitive restriction enzyme; it is of course understood that this may involve one or more restriction enzymes, depending on the sites which were selected to be protected by the formation of the triplexes.

This digestion leads to the formation of linear double-strand DNA from all the plasmids which contained sites protected from methylation. In contrast, the other plasmids remain intact.

The restriction enzymes used must have sites which are sufficiently frequent so that the probability of finding them in the targeted inserts, whose length varies from 200 to 250 nt, is high; accordingly, restriction enzymes will be preferably used whose recognition sequence contains 4 nucleotides.

In addition, if several enzymes have to be used, it is preferable that they are active under the same, in particular buffer, conditions; this will avoid having to carry out a digestion in several steps, although this is not excluded from the scope of the present invention.

As has been indicated above, two enzymes were used in the examples which will follow; they are MspI and HaeIII.

The last step, the elimination or separation of the linear double-strand DNA molecules, is optional. It is possible, in some cases, to use procedures allowing the separation of the circular double-strand plasmids from the linear double-strand DNA fragments; some of these procedures were mentioned above. However, it is also possible to eliminate by digesting the linear double-strand DNAs in particular by hydrolyzing them with exonucleases, in particular exonuclease III which hydrolysis DNA in the 5'–3' direction.

This digestion step has the advantage of avoiding possible rearrangements when the linear DNA is transformed in bacteria.

This step is more particularly advantageous for eliminating the repetitiveness in cDNA libraries. More generally, it may be used for eliminating any undesirable sequence from a library. The choice of undesirable sequences may be made:

after analyzing a sample of clones (for example 2000 to 3000 clones), deliberately in order to automatically eliminate certain sequences which conventionally contaminate cDNA libraries (ribosomal or mitochrondrial sequences).

In particular, the method according to the present invention makes it possible to eliminate the most repetitive clones, for example the TOP20s, that is to say the clones corresponding to the 20 most abundant sequences, from each library. The calculations carried out have shown that the elimination of the TOP20s from a cDNA library made it possible to considerably increase the relative representation of the remaining clones.

In this embodiment, it will be possible, for example, to adjust the molar ratios between each oligonucleotide used and its target sequence, in order to eliminate various sequences simultaneously and optimally.

It is also possible to use the method according to the invention either to normalize the distribution of sequences in a library, or to randomly eliminate clones.

In the case of normalization, the protocol applied might be the following:

1) produce a plasmid preparation (double-strand) from the library,
2) from the plasmid preparation, synthesize single-strand PNA or DNA fragments covering all the inserts, or some of them,
3) use the single-strand DNA fragments as template for the formation of triplexes catalyzed by RecA or directly form the triplexes with said PNA fragments,
4) methylate the sequences not engaged in triplexes,
5) break the triplexes,
6) digest the plasmid preparations with one or two methylation-sensitive restriction enzymes (enzymes whose restriction site contains 4 bases),
7) digest the linearized DNAs with exonuclease,
8) clone and propagate the intact plasmids.

In the case of the random elimination of clones, the manipulation would consist in:

1) ordering 2000 to 4000 clones,
2) grouping together these clones to produce from these clones single-strand DNA probes,
3) using the single-strand DNAs to eliminate the corresponding sequences from the original library,
4) subsequently, 2 to 4000 new clones may be ordered, sequenced and likewise used to eliminate the corresponding sequences from the residual library.

The present invention finally relates to the cDNA libraries thus obtained using the method described above.

The examples below will make it possible to demonstrate other characteristics and advantages of the present invention.

FIG. 1 schematically represents the method according to the present invention.

Figure 2B:
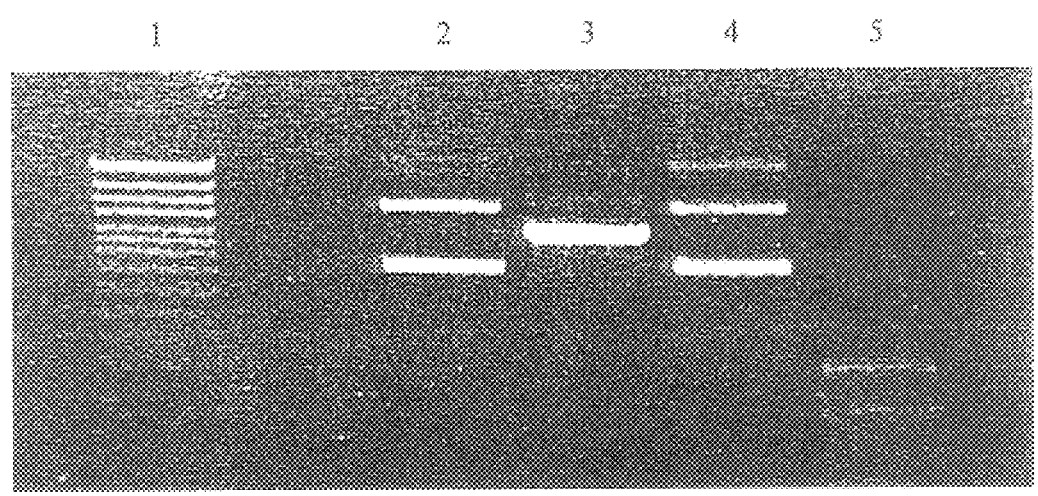

FIGS. 2A and 2B presents the results obtained on agarose gel, for the linearization of a circular plasmid by targeted digestion on a restriction site, using the method according to the invention.

FIG. 2A, results using CL1 (SEQ ID NO: 1);

FIG. 2B, results using clone CL13 (SEQ ID NO: 2).

Figure 3A:
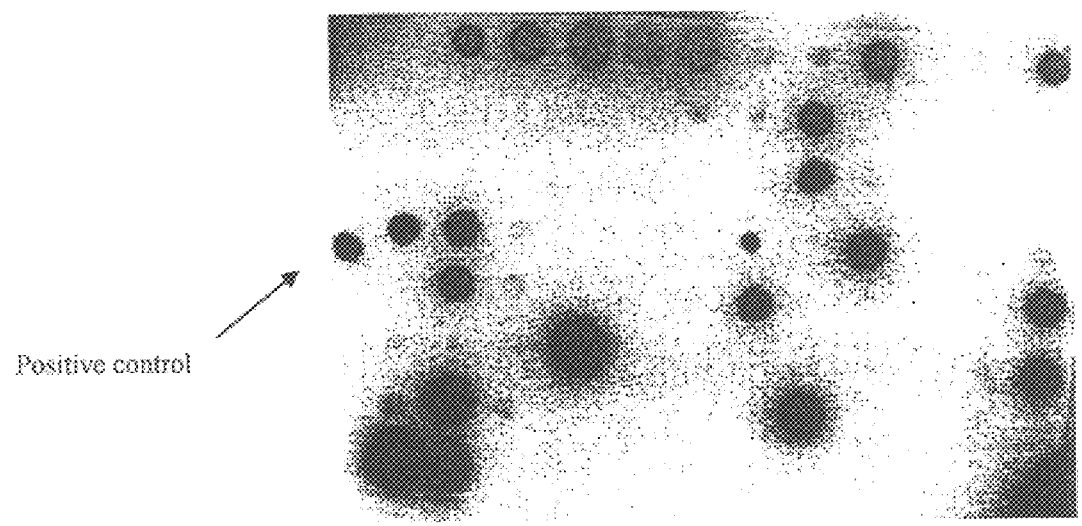
Figure 3B:
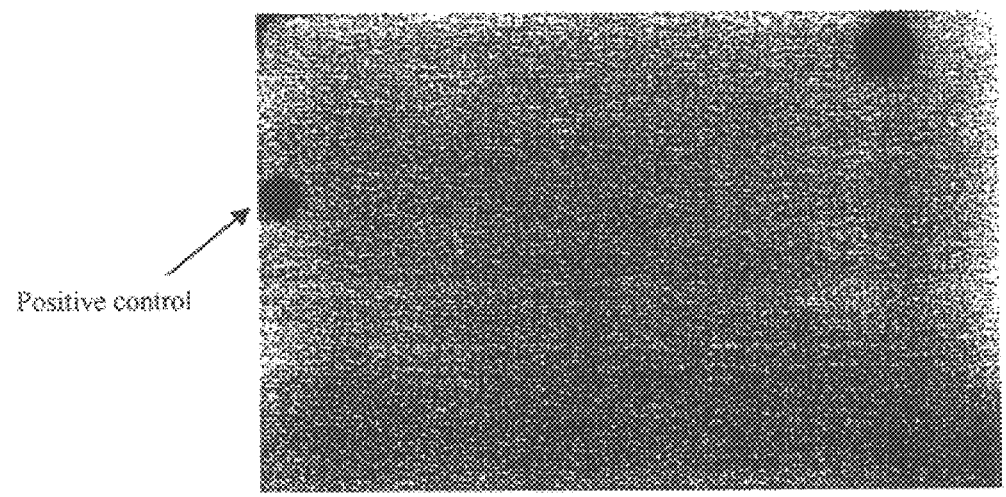

FIGS. 3A and 3B presents the results of elimination of a target plasmid from a mixture of plasmids, using the method according to the invention. FIG. 3A, hybridization of $^{32}$P-phosphorylated oligonucleotide (OCL1 (SEQ ID NO: 3)) specific for target plasmid CL1 (SEQ ID NO: 1) prior to using the method according to the invention; FIG. 3B, hybridization of $^{32}$P-phosphorylated oligonucleotide (OCL1 (SEQ ID NO: 3)) specific for target plasmid CL1 (SEQ ID NO: 1) after using the method according to the invention.

FIG. 4 presents the sequences of the inserts of two target plasmids CL1 (SEQ ID NO: 1) and CL13 (SEQ ID NO: 2). The oligonucleotides used to carry out the method of elimination according to the invention, OCL1 (SEQ ID NO: 3) and OCL13 (SEQ ID NO: 4) respectively, are underlined; the restriction sites used, MspI and HaeIII respectively, are represented in bold type.

Strategy for Protection and Elimination by RecA

This figure summarizes the procedure used to eliminate specific sequences from a cDNA library using the RecA protein. It shows the effects of the protocol on the plasmid for one of the targeted clones among the TOP20s (plasmid A), and on the plasmid for a nontargeted clone (plasmid B). After formation of the presynaptic filament, the oligonucleotide-RecA complex is mixed with the double-strand plasmid DNA preparation. Since the oligonucleotide is chosen specifically to hybridize to those of the 20 most abundant sequences which correspond to the insert of plasmid A, the latter can form a triplex with the oligonucleotide complexed with the protein, unlike plasmid B. Methylation modifies all the sites for the restriction enzyme chosen (hatched regions) on plasmids A and B, with the exception of the site in plasmid A protected by the formation of the triplex. After denaturation of the RecA protein, the addition of the restriction enzyme generates the linearization of plasmid A, whereas plasmid B remains circular. The final step is a hydrolysis of plasmid A (linearized) with exonuclease. This makes this linearized plasmid shorter, and certainly nonclonable. This step will not affect the circular plasmid B.

Materials and Methods

During the experimental procedure, the following materials are used:

RMB (RecA and Methylase buffer): 250 mM Tris-acetate, 40 mM magnesium acetate.

RecA protein: Promega. No. M1692. A 2.58 mg/ml.
(γS)ATP: Adenosine-5'-O-(3-thiotriphosphate), 10 mM. Boehringer Manheim. No. 83317521-12.
BSA: Bovine Serum Albumine, 10 mg/ml. New England Biolabs. Provided with the enzymes.
DTT: 100 mM.
Magnesium acetate: 80 mM.
HaeIII methylase. New England Biolabs. No. 224L. 10,000 U/ml.
MspI methylase. New England Biolabs. No. 215L. 5000 U/ml.
SAM: S-adenosylmethionine, 32 mM. New England Biolabs. Provided with the enzymes.
Restriction enzyme HaeIII. New England Biolabs. No. 108L. 10,000 U/ml.
Restriction enzyme MspI. New England Biolabs. No. 106L. 20,000 U/ml.
Exonuclease III. New England Biolabs. No. 206L. 100,000 U/ml.
Ampicillin. Sigma. No. A-9518.
X-gal. Sigma. No. B-9146.
ITPG. Sigma. No. I-6758.
(COLONY PICKER. Hybaid).

The various protocols used during the procedure are the following:

Protocol 1: Formation of the presynaptic filament

1 μl of RMB, 6.25 μg of RecA protein and 160 ng of oligonucleotide are added to a 1.5 ml Eppendorf tube and adjusted to 9 μl with distilled water. The mixture is stirred gently by pipetting and incubated for one minute at 37° C. 1 μl of (γS)ATP (kept at −80° C.) is added and the mixture is incubated for 10 minutes at 37° C. The oligonucleotide and the RecA protein are mixed in a molar ratio of 3:1, taking into account the fact that one monomer of the protein binds to the nucleotide sequence every 3 bases.

Protocol 2: Formation of the triplex

1 μg of plasmid DNA, 2 μl of RMB, 2.7 μl of DTT and 3 μl of BSA are mixed gently in a 1.5 ml Eppendorf tube and adjusted to 17 μl with distilled water. This mixture is added to the preceding solution and the mixture is incubated for 40 minutes at 37° C., Protocol 3: Methylation 20 units of methylase, magnesium acetate and SAM in final concentrations of 8 mM and 80 mM, respectively, are added to the preceding solution, and the mixture is adjusted to 40 μl with distilled water. It is incubated for 45 minutes at 37° C. At the end of the reaction, the solution is heated for 15 minutes at 65° C. in order to stop the methylation and to denature the oligonucleotide-RecA complex. The solution is then purified by phenol extraction followed by precipitation with 0.3 M sodium acetate in ethanol.

Protocol 4: Digestion with the restriction enzyme

The pellet is taken up in 10 μl of distilled water. 2.5 μl of the 10× enzyme buffer and 20 units of the restriction enzyme are added and the mixture is adjusted to 25 μl with distilled water and incubated for one hour at 37° C. Finally, the solution is purified by phenol extraction followed by precipitation with 0.3 M sodium acetate in ethanol.

Protocol 5: Digestion with exonuclease III

The pellet is taken up in 10 μl of distilled water. 5 μl of the 10× enzyme buffer and 400 units of exonuclease are added and the mixture is adjusted to 50 μl with distilled water. It is incubated for 45 minutes at 37° C. The DNA is purified by phenol extraction and precipitated with ethanol in the presence of 0.3 M sodium acetate. The pellet is taken up in 10 μl of distilled water.

The DNA thus obtained is used to transform competent bacteria.

RESULTS

Linearization of a Circular Plasmid by Targeted Digestion on a Restriction Site Example I: Efficiency of the Use of the RecA Protein This experiment is carried out on two cDNA clones (CL1 (SEQ ID NO: 1) and CL13) (SEQ ID NO: 2) which are in different quantities in a pancreas library. One of the two clones (CL1(SEQ ID NO: 1)) corresponds to a cDNA whose quantity is 15%, the sequence corresponding to the other clone (CL13(SEQ ID NO: 2)) is present at 1% in the library. The oligonucleotides OCL1 (SEQ ID NO: 3) and OCL13 (SEQ ID NO: 4) were chosen under the conditions described above; they contain respectively the MspI (C*CGG) and HaeIII (GG*CC) restriction sites, at positions 16 and 473 respectively on the sequences of the corresponding clones; the targeted sequences and the oligonucleotides OCL1 (SEQ ID NO: 3) and OCL13 (SEQ ID NO: 4) are represented in FIG. 4. The RecA protein forms a complex with oligonucleotides OCL1 (SEQ ID NO: 3) and OCL13(SEQ ID NO: 4). The presynaptic filaments obtained are then mixed with the plasmid preparations obtained from clones CL1 (SEQ ID NO: 1) and CL13 (SEQ ID NO: 2) respectively. The results on a 0.8% agarose gel (FIGS. 2A and 2B) show that for the products of the elimination procedure, plasmids protected by RecA, methylated and then digested with a restriction enzyme (lanes 3), the plasmid DNA was linearized, and shows a migration profile corresponding to a single 3 Kb band which migrates between that for the supercoiled DNA and that for the circular DNA. The migration profiles for the plasmids not protected, then methylated and digested with a restriction enzyme (lanes 4) and for the native plasmids (lanes 2) are similar, which shows that the methylation conditions are sufficient to modify all the nonprotected restriction sites; no digestion takes place. The multitude of bands which are observed for the plasmids not protected and not methylated, but digested with the restriction enzymes (lanes 5), is due to the fact that the sites for the enzymes MspI and HaeIII are present in 13 and 14 copies respectively in the cloning vector (BlueScript II SK(-), Stratagene, No. 212206). This brings about the cleavage of the vector at several sites.

Specific Elimination of a Targeted Plasmid from a Mixture of Plasmids

Example II: Efficiency of the Use of the RecA Protein: Two Different Model Systems To test the efficiency of the elimination of an abundant clone using the RecA protein, two experiments were carried out.

In the first experiment, the double-strand DNA treated consists of one of our preceding two plasmid preparations (CL1 (SEQ ID NO: 1) and CL13(SEQ ID NO: 2)), mixed with a preparation of plasmids corresponding to a cloning vector (pBSSK). The two clones 1 and 13 were separately mixed with the plasmid pBSSK in a proportion equivalent to their abundance in the pancreas library, that is to say 15% and 1% respectively. The elimination according to the invention using the RecA protein was carried out using oligonucleotides OCL1 (SEQ ID NO: 3) and OCL13(SEQ ID NO: 4), according to the procedure described above. The final product was used to transform electrocompetent bacteria (Epicurian Coli SURE, Stratagene No. 2000227) and the solution obtained spread on LB agar plates with ampicillin, X-gal and ITPG. The number of recombinant clones (white colonies containing inserts corresponding to the sequences of clones 1 (SEQ ID NO: 1) or 13 (SEQ ID NO: 2)) was counted before and after elimination treatment. For clone 1 (SEQ ID NO: 1), the percentage of recombinant clones is 9% before treatment and 1.4% after elimination of this clone. For clone 13 (SEQ ID NO: 2), the drop is from 1.5% to 0.28%. These two tests show an elimination efficiency of 84%.

In the second experiment, a preparation of plasmids corresponding to the entire pancreas library constituted the double-strand DNA treated by the elimination procedure. The latter was carried out with oligonucleotide OCL1 (SEQ ID NO: 3), with the aim of eliminating clone CL1 (SEQ ID NO: 1)from the total library.

The human pancreas cDNA library is a library corresponding to the 5' ends of the pancreas mRNAs. Thus, since oligonucleotide OCL1 (SEQ ID NO: 3) is chosen near the 5' end (position 16), all the clones corresponding to the 5' end of this messenger ought to be eliminated. In a dT primed cDNA library, the same manipulation may be carried out on the 3' end of the messenger RNAs. On the other hand, in the case of a randomly primed library, the choice of the oligonucleotides is more delicate. This may be overcome either by finding, with the aid of computer software, homologies between the sequences and by choosing the oligonucleotides in the conserved region, or by synthesizing single-strand DNA probes from inserts using sequences of the multiple cloning site as primers.

After formation of the presynaptic filament with oligonucleotide OCL1 (SEQ ID NO: 3) and protection, the methylation was carried out with MspI methyltransferase. The enzyme MspI was then added and the digestion mixture treated with exonuclease III. Electrocompetent bacteria were transformed with the final product and spread on LB agar plates. In theory, all the plasmids in the library, except those carrying the sequence corresponding to the insertion of clone 1, will be completely methylated, and therefore not digested with the enzyme MspI. PCRs (Polymerase Chain Reaction) were carried out on 96 recombinant colonies using as amplification primers the conventional "reverse" and "universal" primers, in order to take the inserts out of the plasmids. The PCR products were spotted on positively charged nylon filters (Amersham Life Sciences), and the filters thus obtained hybridized using the P32-phosphorylated oligonucleotide (OCL1(SEQ ID NO: 3)) specific for the clone of interest (CL1(SEQ ID NO: 1)). The results of this experiment (FIGS. 3A and 3B) show an elimination efficiency of 85%: the number of positive signals drops from 21 before the treatment to 3 after elimination of the clone in question.

REFERENCES

Adams et al. (1995) "Initial assessment of human gene diversity and expression patterns based upon 83 million nucleotides of cDNA sequence" Nature, 377 supp, 3–174.

Britten R. J., Grahan D. E., Neufeld B. R. (1974) "Analysis of repeating DNA sequences by reassociation" Method in Enzymol, 29, 363–418.

Davidson E. H. and Britten R. J. (1979) "Regulation of Gene Expression Possible Role of Repetitive Sequences". Science 204, 1052–1059.

Koob M., Barbiewicz A., Ku J., Szybalski W. (1992) "RecA-AC: single site cleavage of plamids and chromosomes at any predetermined restriction site" Nucleic Acids Res., 21, 5831–5836.

Lanfranchi et al. (1985) "A new method for the construction of 3'-end specific cDNA libraries and its application for the identification of 4370 expressed sequence tags (ESTs) from human skeletal muscle" Genome Science & Technology, 1, 63.

Patanjali S. R., Parimoo S. and Weissman S. M. (1991) "Construction of a uniform abundance (normalized) cDNA library" PNAS 8, 1943–1947.

Sasaki Y. F., Ayusawa D. and Orshi M. (1994) "Construction of a normalized cDNA library by introduction of a semi-solid RNA-cDNA hybridization system" NAR 22, 907–922.

Soares M. B. and Efstratiadis A. (1995) "Method for construction of normalized cDNA library" PCT-US 94/10821.

Soares M. B., Fatima Bonaldo F., Jelene P., Su L., Lawton L. and Efstratiadis A. (1994) "Construction and characterization for normalized cDNA library" PNAS 91, 9228–9232.

Veselkov A. G., Demidov V. V., Frank-Kamenetskii M. D., Nielsen P. C. (1996) "PNA as a rare genome-cutter", Nature 379, 214.

Weisman S. M. (1987) "Molecular genetic techniques for mapping the human genome" Mol Biol Med, 4, 133–143.

Young B. D. et Anderson M. L. M (1985) in Nucleic acid hybridization, a practical approach (Yames B. D. and Higgins S. J. ed), 47–72.

What is claimed is:

1. A method for selecting nucleic acids lacking at least one target sequence from a population of double stranded nucleic acids wherein said population includes double stranded nucleic acids comprising said target sequence and double stranded nucleic acids lacking said target sequence, said method comprising:
contacting said population of double stranded nucleic acids with at least one nucleic acid which hybridizes to said at least one target sequence under conditions in which said at least one nucleic acid which hybridizes to said at least one target sequence forms a triplex with said double stranded nucleic acids containing said at least one target sequence, wherein said at least one nucleic acid which hybridizes to said at least one target sequence has at least one restriction site recognized by a methylation sensitive restriction enzyme;
performing a methylation reaction on said population of double stranded nucleic acids;
dissociating said at least one nucleic acid which hybridizes to said at least one target sequence from said at least one target sequence;
performing a restriction digest with at least one methylation sensitive enzyme which cleaves at said at least one restriction site, wherein said double stranded nucleic acids containing said target sequence are cleaved by said at least one restriction enzyme while double stranded nucleic acids lacking said at least one target sequence are not cleaved by said at least one restriction enzyme; and
selectively recovering double stranded nucleic acids which were not cleaved by said at least one restriction enzyme.

2. The method of claim 1 wherein said selectively recovering step comprises introducing said population of double stranded nucleic acids into a suitable host cell wherein double stranded nucleic acids which were cleaved by said restriction enzyme do not replicate in said host cell and double stranded nucleic acids which were not cleaved by said restriction enzyme replicate in said host cell.

3. The method of claim 1, wherein said double stranded nucleic acids are plasmids.

4. The method of claim 1, wherein said at least one nucleic acid which hybridizes to said at least one target sequence is a peptide nucleic acid.

5. The method of claim 1, wherein said population of double stranded nucleic acids is a DNA library.

6. The method of claim 1, wherein said population of double stranded nucleic acids is a cDNA library.

7. The method of claim 1, wherein nucleic acids lacking one target sequence are selectively recovered.

8. The method of claim 1, wherein nucleic acids lacking several target sequences are selectively recovered.

9. The method of claim 1, wherein nucleic acids lacking a target sequence that is abundant are selectively recovered.

10. The method of claim 1, wherein nucleic acids lacking several target sequences that are abundant are selectively recovered.

11. The method of claim 1, wherein the triplex is formed in the presence of divalent cations.

12. The method of claim 1, wherein the triplex is formed in the presence of ATPγS.

13. The method of claim 1, wherein the methylation step is carried out by methyltransferases.

14. The method of claim 1, wherein the methylation sensitive restriction enzyme is selected from the group consisting of HaeIII and MspI.

15. The method of claim 1, wherein the nucleic acids which were cleaved by said restriction enzyme are eliminated by hydrolysis.

16. The method of claim 15, wherein the hydrolysis is carried out by an exonuclease.

17. A method for selecting nucleic acids lacking at least one target sequence from a population of double stranded nucleic acids wherein said population includes double stranded nucleic acids comprising said at least one target sequence and double stranded nucleic acids lacking said at least one target sequence, said method comprising:

contacting said population of double stranded nucleic acids with at least one single stranded nucleic acid which hybridizes to said at least one target sequence, wherein said at least one single stranded nucleic acid which hybridizes to said at least one target sequence has at least one restriction site recognized by a methylation sensitive restriction enzyme and is complexed with a protein which facilitates formation of a triplex comprising said at least one single stranded nucleic acid and said at least one target sequence;

performing a methylation reaction on said population of double stranded nucleic acids;

dissociating said at least one single stranded nucleic acid which hybridizes to said at least one target sequence from said at least one target sequence;

performing a restriction digest with at least one methylation sensitive enzyme which cleaves at said at least one restriction site, wherein said double stranded nucleic acids containing said at least one target sequence are cleaved by said restriction enzyme while double stranded nucleic acids lacking said at least one target sequence are not cleaved by said at least one restriction enzyme; and selectively recovering double stranded nucleic acids which were not cleaved by said at least one restriction enzyme.

18. The method of claim 17 wherein said selectively recovering step comprises introducing said population of double stranded nucleic acids into a suitable host cell wherein double stranded nucleic acids which were cleaved by said at least one restriction enzyme do not replicate in said host cell and double stranded nucleic acids which were not cleaved by said at least one restriction enzyme replicate in said host cell.

19. The method of claim 17 wherein said double stranded nucleic acids are plasmids.

20. The method of claim 17, wherein said at least one nucleic acid which hybridizes to said at least one target sequence is a peptide nucleic acid.

21. The method of claim 17, wherein said population of double stranded nucleic acids is a DNA library.

22. The method of claim 17, wherein said population of double stranded nucleic acids is a cDNA library.

23. The method of claim 17, wherein nucleic acids lacking one target sequence are selectively recovered.

24. The method of claim 17, wherein nucleic acids lacking several target sequences are selectively recovered.

25. The method of claim 17, wherein nucleic acids lacking a target sequence that is abundant are selectively recovered.

26. The method of claim 17, wherein nucleic acids having several target sequences that are abundant are separated from nucleic acids lacking said target sequences.

27. The method of claim 17, wherein the triplex is formed in the presence of divalent cations.

28. The method of claim 17, wherein the triplex is formed in the presence of ATPγS.

29. The method of claim 17, wherein the methylation step is carried out by methyltransferases.

30. The method of claim 17, wherein the methylation sensitive restriction enzyme is selected from the group consisting of HaeIII and MspI.

31. The method of claim 17, wherein the nucleic acids which were cleaved by said at least one restriction enzyme are eliminated by hydrolysis.

32. The method of claim 31, wherein the hydrolysis is carried out by an exonuclease.

33. The method of claim 17, wherein the protein which facilitates formation of a triplex comprising said at least one single stranded nucleic acid and said at least one target sequence is RecA.

* * * * *